(12) United States Patent
Pauze

(10) Patent No.: US 8,088,114 B1
(45) Date of Patent: Jan. 3, 2012

(54) UROSTOMY BAG COVER SYSTEM

(76) Inventor: Marilyn B. Pauze, Largo, FL (US)

( * ) Notice: Subject to any disclaimer, the term of this patent is extended or adjusted under 35 U.S.C. 154(b) by 755 days.

(21) Appl. No.: 12/079,091

(22) Filed: Mar. 25, 2008

(51) Int. Cl.
*A61F 5/44* (2006.01)
(52) U.S. Cl. .................. 604/335; 604/327; 604/345
(58) Field of Classification Search .................. 604/262, 604/317, 327–353; 383/44, 49
See application file for complete search history.

(56) References Cited

U.S. PATENT DOCUMENTS

| | | | | |
|---|---|---|---|---|
| 3,415,299 A | * | 12/1968 | Hinman, Jr. et al. | 206/324 |
| 4,085,752 A | * | 4/1978 | Canale | 604/370 |
| 4,581,763 A | * | 4/1986 | Olsen | 383/49 |
| 5,653,701 A | * | 8/1997 | Millman | 604/345 |

* cited by examiner

Primary Examiner — Tatyana Zalukaeva
Assistant Examiner — Benedict L Hanrahan

(57) ABSTRACT

A bag cover is fabricated of a flexible material. The bag cover has a rear sheet with a hole adjacent to a top edge. The rear sheet has a downwardly extending projection formed at a bottom edge. The cover has a front sheet overlying the rear sheet. A top edge is essentially midway between top and bottom edges of the rear sheet. A pocket receives and supports a bag. A slit is provided in the rear sheet between an upper edge and the hole. Facing fasteners are provided on the rear sheet adjacent to the slit. The facing fasteners are adapted to be separated to separate a bag from the cover. A fixed patch of hook and loop fasteners is provided on an upper surface of the projection. An overlying removable patch is provided. The patches are adapted to receive a cylindrical portion of a bag.

1 Claim, 3 Drawing Sheets

UROSTOMY BAG COVER SYSTEM

BACKGROUND OF THE INVENTION

Field of the Invention

The present invention relates to a urostomy/colostomy bag cover system and more particularly pertains to precluding the twisting of a tubing portion with respect to a bag portion of a urostomy/colostomy bag with attendant flow stoppage in a safe, convenient and economical manner.

SUMMARY OF THE INVENTION

In view of the disadvantages inherent in the known types of urostomy/colostomy bag covers of known designs and configurations now present in the prior art, the present invention provides an improved urostomy/colostomy bag cover system. As such, the general purpose of the present invention, which will be described subsequently in greater detail, is to provide a new and improved urostomy/colostomy bag cover system and method which has all the advantages of the prior art and none of the disadvantages.

To attain this, the present invention essentially comprises a urostomy/colostomy bag cover system. First provided is a fluid impervious urostomy/colostomy bag. The urostomy/colostomy bag has an upper bag portion. The upper bag portion is provided in a generally flat, rectangular configuration. The urostomy/colostomy bag has a top edge. The urostomy/colostomy bag has a bottom edge. The urostomy/colostomy bag also has side edges. The side edges are provided between the top and bottom edges. The bag portion is fabricated of a flexible plastic. The bag portion has a front panel. The bag portion has a rear panel. The bag portion has a peripheral heat seal. The heat seal is provided along the upper and side edges. The heat seal is further provided along a majority of the lower edge. The lower edge has a central opening. The rear panel has a circular opening. The circular opening is provided adjacent to the top edge. The bag portion has a stiffening ring. The bag portion also has radial fingers. In this manner the urostomy/colostomy bag is coupled to a patient. Further in this manner human waste is adapted to flow into the bag portion. The urostomy/colostomy bag also has a lower drain portion. The bag has a fixed component. The fixed portion is secured in the central opening of the bag portion. The urostomy/colostomy bag has a axially rotatable cylindrical portion. The urostomy/colostomy bag further has a valve. In this manner the valve may be selectively opened and closed in response to the rotation of the cylindrical portion.

A urostomy/colostomy bag cover is provided. The urostomy/colostomy bag cover is fabricated of a flexible, washable fabric. The urostomy/colostomy bag cover is provided in a generally flat, rectangular configuration. The urostomy/colostomy bag cover has a rear sheet. The rear sheet has a top edge. The rear sheet has a bottom edge. The rear sheet has side edges. The side edges are provided between the top and bottom edges. The rear sheet has a hole. The hole is provided adjacent to the top edge. In this manner the stiffening ring and radial fingers may be received. Further in this manner the urostomy/colostomy bag may be releasably coupled to the urostomy/colostomy bag cover. The rear sheet also has a downwardly extending projection. The downwardly extending projection is integrally formed with the bottom edge of the rear sheet.

The urostomy/colostomy bag cover also has a front sheet. The front sheet has a top edge. The front sheet has a bottom edge. The front sheet has side edges. The side edges are provided between the top and bottom edges. The front sheet overlies the rear sheet. The top edge of the front sheet is essentially midway between the top and bottom edges of the rear sheet. The front sheet has stitching. The stitching couples the side edges and a portion of the bottom edges of the front and rear sheets. In this manner a central passageway is formed for the drain portion of the urostomy/colostomy bag. The rear sheet has a front surface. The front sheet has a rear surface. In this manner a pocket is defined. The pocket receives and supports the urostomy/colostomy bag.

Further provided is a slit. The slit is provided in the rear sheet between the upper edge and the hole. The rear sheet has facing small patches of hook and loop fasteners. The hook is provided adjacent to the slit. The patches are adapted to be separably coupled. In this manner the urostomy/colostomy bag and the cover are secured together. The patches are adapted to be separated. In this manner the urostomy/colostomy bag and the cover may be separated.

Provided last are facing large patches of hook and loop fasteners. The facing large patches include a fixed patch. The fixed patch is stitched to the upper surface of the projection. The facing large patches include an overlying removable patch. The fixed and removable patches are adapted to receive the cylindrical portion of the urostomy/colostomy bag. The cylindrical portion is provided parallel with the side edges of the lower sheet. A line of stitching is provided. The line of stitching joins the large patches along side edges of the large patches parallel with the side edges of the lower sheet. In this manner, when the urostomy/colostomy bag is located in the pocket with the cylindrical portion between the large patches, any twisting of the urostomy/colostomy bag will cause a concurrent twisting of the cylindrical portion. Further in this manner flow from the urostomy/colostomy bag will be stopped.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved urostomy/colostomy bag cover system which has all of the advantages of the prior art urostomy/colostomy bag covers of known designs and configurations and none of the disadvantages.

It is another object of the present invention to provide a new and improved urostomy/colostomy bag cover system which may be easily and efficiently manufactured and marketed.

It is further object of the present invention to provide a new and improved urostomy/colostomy bag cover system which is of durable and reliable constructions.

An even further object of the present invention is to provide a new and improved urostomy/colostomy bag cover system which is susceptible of a low cost of manufacture with regard to both materials and labor, and which accordingly is then susceptible of low prices of sale to the consuming public, thereby making such urostomy/colostomy bag cover system economically available to the buying public.

Even still another object of the present invention is to provide a urostomy/colostomy bag cover system for precluding the twisting of a tubing portion with respect to a bag portion of a urostomy/colostomy bag with attendant flow stoppage in a safe, convenient and economical manner.

Lastly, it is an object of the present invention to provide a new and improved urostomy/colostomy bag cover system. A bag cover is fabricated of a flexible material. The bag cover has a rear sheet with a hole adjacent to a top edge. The rear sheet has a downwardly extending projection formed at a bottom edge. The cover has a front sheet overlying the rear sheet. A top edge is essentially midway between top and bottom edges of the rear sheet. A pocket receives and supports a bag. A slit is provided in the rear sheet between an upper edge and the hole. Facing fasteners are provided on the rear sheet adjacent to the slit. The facing fasteners are adapted to be separated to separate a bag from the cover. A fixed patch of hook and loop fasteners is provided on an upper surface of the projection. An overlying removable patch is provided. The patches are adapted to receive a cylindrical portion of a bag.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
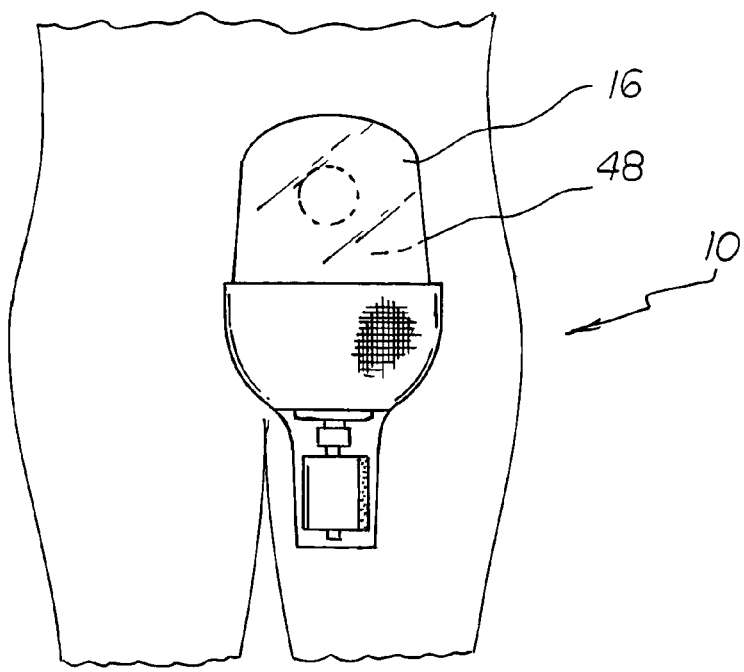
FIG. 1 is a front elevational view of a urostomy/colostomy bag system constructed in accordance with the principles of the present invention.
Figure 2:
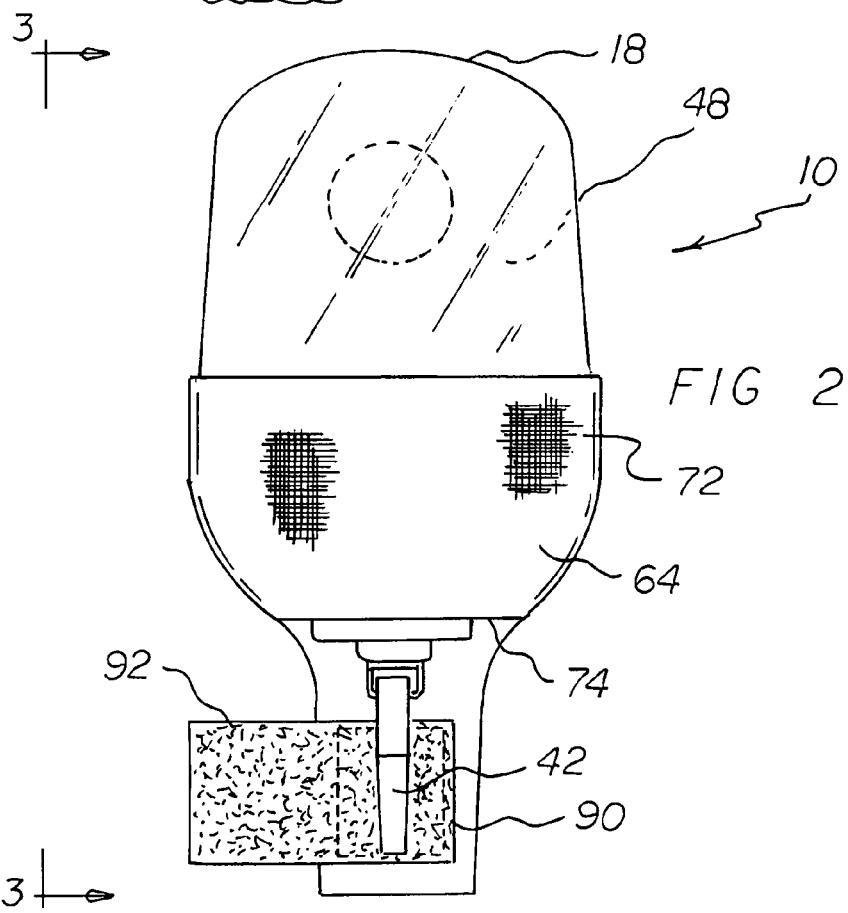
FIG. 2 is an enlarged front elevational view of the system shown in FIG. 1.
Figure 3:
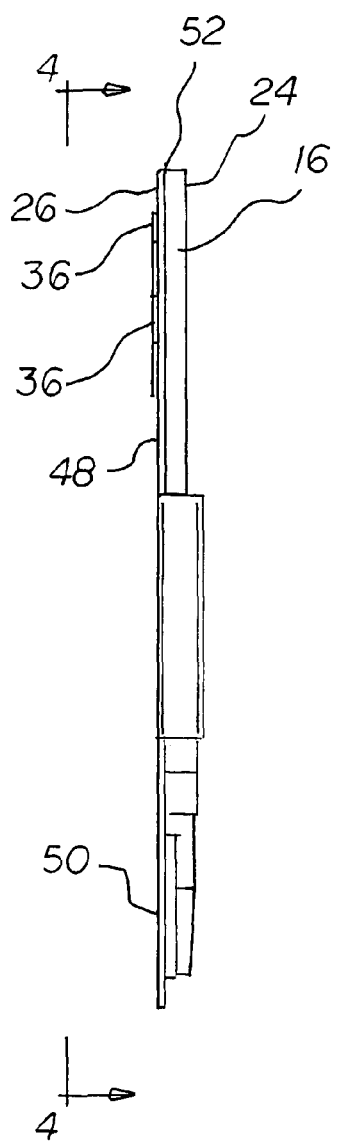
FIG. 3 is a side elevational view taken along line 3-3 of FIG. 2.
Figure 4:
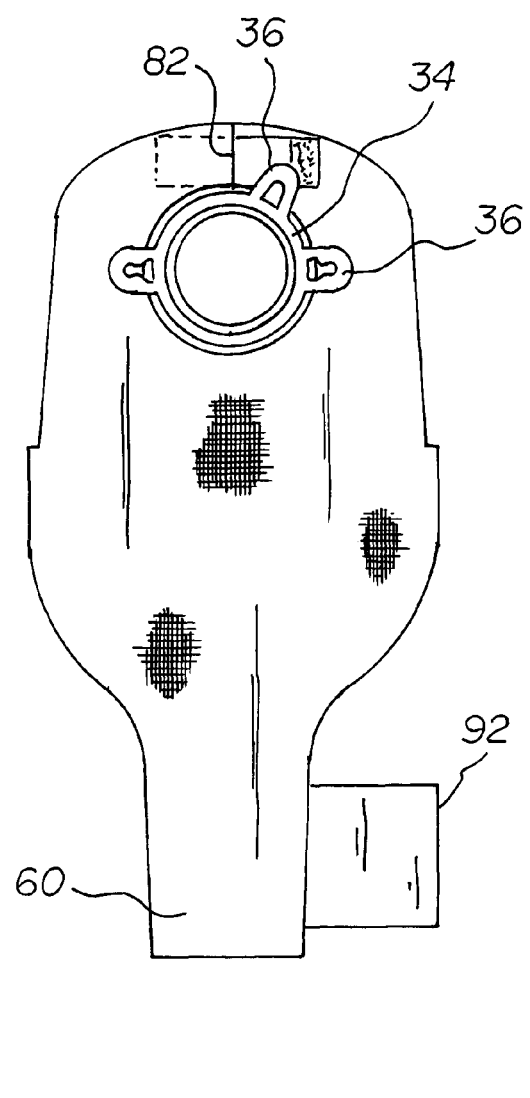
FIG. 4 is a rear elevational view taken along line 4-4 of FIG. 3.
Figure 5:
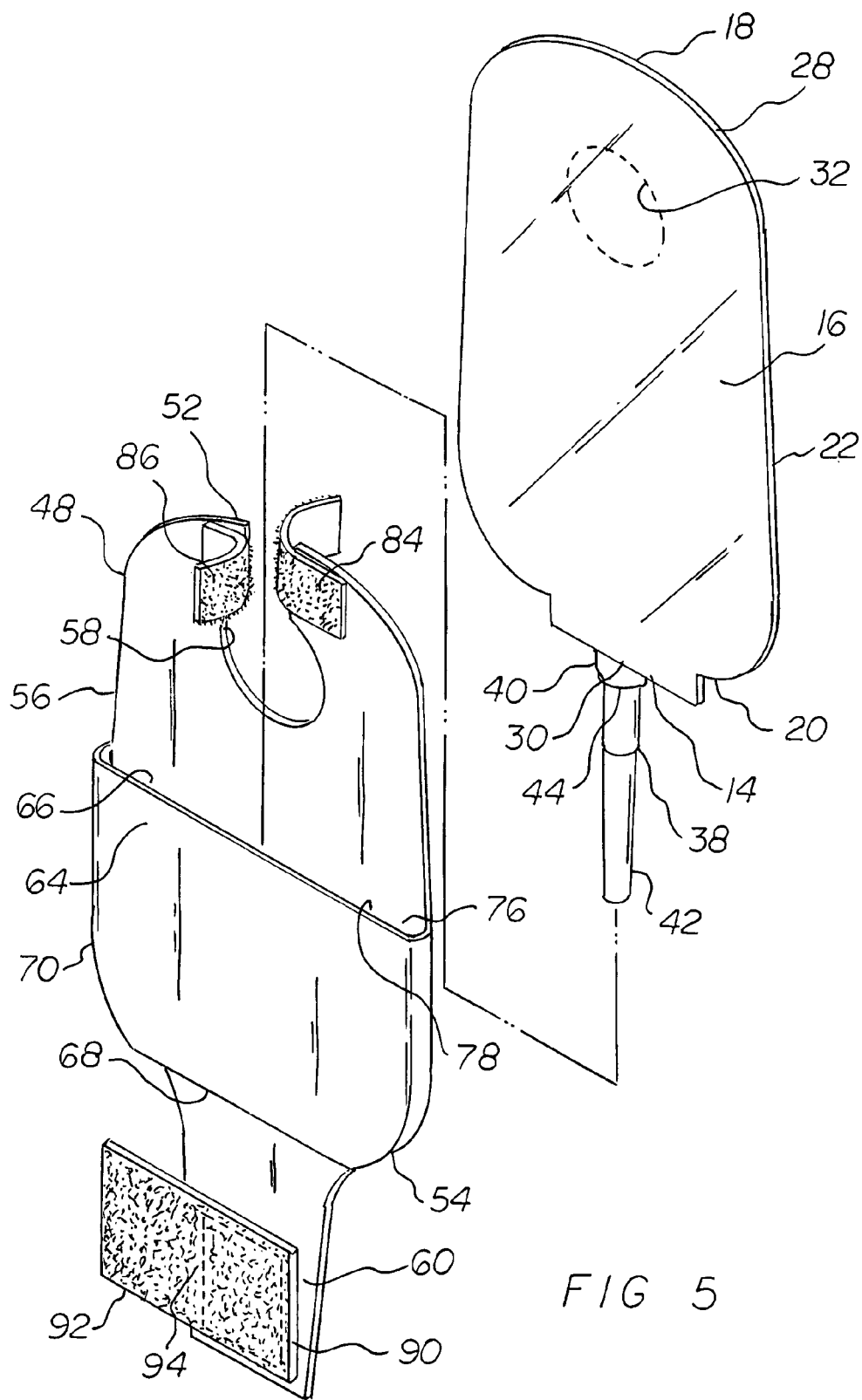
FIG. 5 is an exploded perspective illustration of the system of the prior Figures.

With reference now to the drawings, and in particular to FIG. 1 thereof, the preferred embodiment of the new and improved urostomy/colostomy bag cover system embodying the principles and concepts of the present invention and generally designated by the reference numeral 10 will be described.

The present invention, the urostomy/colostomy bag cover system 10 is comprised of a plurality of components. Such components in their broadest context include a bag cover, a slit and facing patches of hook and loop fasteners. Such components are individually configured and correlated with respect to each other so as to attain the desired objective.

First provided is a fluid impervious urostomy/colostomy bag 14. The urostomy/colostomy bag has an upper bag portion 16. The upper bag portion is provided in a generally flat, rectangular configuration. The urostomy/colostomy bag has a top edge 18. The urostomy/colostomy bag has a bottom edge 20. The urostomy/colostomy bag also has side edges 22. The side edges are provided between the top and bottom edges. The bag portion is fabricated of a flexible plastic. The bag portion has a front panel 24. The bag portion has a rear panel 26. The bag portion has a peripheral heat seal 28. The heat seal is provided along the upper and side edges. The heat seal is further provided along a majority of the lower edge. The lower edge has a central opening 30. The rear panel has a circular opening 32. The circular opening is provided adjacent to the top edge. The bag portion has a stiffening ring 34. The bag portion also has radial fingers 36. In this manner the urostomy/colostomy bag is coupled to a patient. Further in this manner human waste is adapted to flow into the bag portion. The urostomy/colostomy bag also has a lower drain portion 38. The urostomy/colostomy bag has a fixed component 40. The fixed component is secured in the central opening of the bag portion. The urostomy/colostomy bag has a axially rotatable cylindrical portion 42. The urostomy/colostomy bag further has a valve 44. In this manner the valve may be selectively opened and closed in response to the rotation of the cylindrical portion as by the user or the health care provider.

A urostomy/colostomy bag cover 48 is provided. The urostomy/colostomy bag cover is fabricated of a flexible, washable fabric. The urostomy/colostomy bag cover is provided in a generally flat, rectangular configuration. The urostomy/colostomy bag cover has a rear sheet 50. The rear sheet has a top edge 52. The rear sheet has a bottom edge 54. The rear sheet has side edges 56. The side edges are provided between the top and bottom edges. The rear sheet has a hole 58. The hole is provided adjacent to the top edge. In this manner the stiffening ring and radial fingers may be received. Further in this manner the urostomy/colostomy bag may be releasably coupled to the urostomy/colostomy bag cover. The rear sheet also has a downwardly extending projection 60. The downwardly extending projection is integrally formed with the bottom edge of the rear sheet.

The urostomy/colostomy bag cover also has a front sheet 64. The front sheet has a top edge 66. The front sheet has a bottom edge 68. The front sheet has side edges 70. The side edges are provided between the top and bottom edges. The front sheet overlies the rear sheet. The top edge of the front sheet is essentially midway between the top and bottom edges of the rear sheet. The front sheet has stitching 72. The stitching couples the side edges and a portion of the bottom edges of the front and rear sheets. In this manner a central passageway 74 is formed for the drain portion of the urostomy/colostomy bag. The rear sheet has a front surface 76. The front sheet has a rear surface. In this manner a pocket 78 is defined. The pocket receives and supports the urostomy/colostomy bag.

The bag cover, in the preferred embodiment, is preferably fabricated of a machine washable material. It is thus adapted to be worn multiple times and washed with the laundry. The utility and economy of the system is thereby extended.

Further provided is a slit 82. The slit is provided in the rear sheet between the upper edge and the hole. The rear sheet has facing small patches 84, 86 of hook and loop fasteners. The hook is provided adjacent to the slit. The patches are adapted to be separably coupled. In this manner the urostomy/colostomy bag and the cover are secured together. The patches are adapted to be separated. In this manner the urostomy/colostomy bag and the cover may be separated.

Provided last are facing large patches 90, 92 of hook and loop fasteners. The facing large patches include a fixed patch 90. The fixed patch is stitched to the upper surface of the projection. The facing large patches include an overlying removable patch 92. The fixed and removable patches are adapted to receive the cylindrical portion of the urostomy/colostomy bag. The cylindrical portion is provided parallel with the side edges of the lower sheet. A line of stitching 94 is provided. The line of stitching joins the large patches along side edges of the large patches parallel with the side edges of the lower sheet. In this manner, when the urostomy/colostomy bag is located in the pocket with the cylindrical portion between the large patches, any twisting of the urostomy/colostomy bag will cause a concurrent twisting of the cylindrical portion. Further in this manner flow from the urostomy/colostomy bag will be stopped.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A bag cover system comprising:
   a fluid impervious urostomy/colostomy bag including an upper bag portion in a generally flat, rectangular configuration having a top edge and a bottom edge with side edges between the top and bottom edges, the bag portion being fabricated of a flexible plastic with a front panel and a rear panel and with a peripheral heat seal along the upper and side edges and along a majority of the lower edge to form a central opening in the lower edge, a circular opening in the rear panel adjacent to the top edge with a stiffening ring and radial fingers for coupling to a patient whereby human waste is adapted to flow into the bag portion, the urostomy/colostomy bag also including a lower drain portion having a fixed portion secured in the central opening of the bag portion and an axially rotatable cylindrical portion with a valve within the fixed portion and rotatable to selectively open and close in response to the rotation of the cylindrical portion;
   a bag cover fabricated of a flexible material including a rear sheet having a hole adjacent to a top edge and a downwardly extending projection formed at a bottom edge;
   the cover also including a front sheet overlying the rear sheet with a top edge being essentially midway between top and bottom edges of the rear sheet and defining a pocket for receiving and supporting a bag;
   a slit in the rear sheet between an upper edge and the hole with facing fasteners on the rear sheet adjacent to the slit adapted to be separated for separating a bag from the cover; and
   facing patches of hook and loop fasteners including a fixed patch on an upper surface of the projection and an overlying removable patch, the patches adapted to receive a cylindrical portion of a bag, the patches including a fixed patch stitched to the upper surface of projection and an overlying removable patch, the fixed and removable patches adapted to receive the cylindrical portion of the urostomy/colostomy bag with the cylindrical portion parallel with the side edges of the lower sheet and with a line of stitching joining the large patches along side edges of the large patches parallel with the side edges of the lower sheet and wherein when the urostomy/colostomy bag is located in the pocket with the cylindrical portion between the large patches whereby any twisting of the urostomy/colostomy bag will cause a concurrent twisting of the cylindrical portion to preclude flow stoppage from the urostomy/colostomy bag.

\* \* \* \* \*